United States Patent [19]
Tajima et al.

[11] Patent Number: 5,968,868
[45] Date of Patent: Oct. 19, 1999

[54] CATALYST FOR USE IN THE ALKYLATION OF ISOALKANES

[75] Inventors: Yoshio Tajima; Fuyuki Aida; Mitsuo Matsuno, all of Yokohama, Japan

[73] Assignee: Nippon Oil Co., Ltd., Tokyo, Japan

[21] Appl. No.: 08/887,764

[22] Filed: Jul. 3, 1997

[30] Foreign Application Priority Data

| Jul. 4, 1996 | [JP] | Japan | 8-193985 |
| Jul. 16, 1996 | [JP] | Japan | 8-205261 |
| Aug. 13, 1996 | [JP] | Japan | 8-231497 |

[51] Int. Cl.$^6$ .......................... B01J 27/138; B01J 31/00; B01J 27/02; B01J 27/06
[52] U.S. Cl. .......................... 502/226; 502/103; 502/104; 502/117; 502/122; 502/125; 502/128; 502/134; 502/168; 502/169; 502/216; 502/224; 502/227
[58] Field of Search .................. 502/103, 104, 502/117, 122, 125, 128, 134, 168, 169, 216, 224, 226, 227

[56] References Cited

U.S. PATENT DOCUMENTS

| 3,717,586 | 2/1973 | Suggitt et al. | 585/721 |
| 4,044,069 | 8/1977 | Bernard et al. | 260/683.47 |
| 4,045,504 | 8/1977 | Brooks et al. | 260/669 R |
| 4,110,251 | 8/1978 | Lauder et al. | 252/442 |
| 4,197,188 | 4/1980 | Antos | 208/139 |
| 4,363,746 | 12/1982 | Capshew | 252/429 B |
| 4,477,587 | 10/1984 | Band | 502/111 |
| 4,650,778 | 3/1987 | Klabunde et al. | 502/8 |
| 5,082,817 | 1/1992 | Albizzati et al. | 502/102 |
| 5,220,095 | 6/1993 | Hommeltoft et al. | 585/721 |
| 5,332,707 | 7/1994 | Karayannis et al. | 502/113 |
| 5,387,567 | 2/1995 | Tajima et al. | 502/103 |
| 5,457,555 | 10/1995 | Tajima et al. | 502/103 |
| 5,556,821 | 9/1996 | Aida et al. | 502/113 |
| 5,574,201 | 11/1996 | Kallenbach | 585/730 |
| 5,633,419 | 5/1997 | Spencer et al. | 502/134 |
| 5,691,264 | 11/1997 | Sacchetti et al. | 502/134 |
| 5,744,681 | 4/1998 | Joly et al. | 585/709 |
| 5,798,314 | 8/1998 | Spencer et al. | 502/115 |

FOREIGN PATENT DOCUMENTS

WO 94/10106  5/1994  WIPO.

*Primary Examiner*—Mark L. Bell
*Assistant Examiner*—Patricia L. Hailey
*Attorney, Agent, or Firm*—Akin, Gump, Strauss, Hauer & Feld, L.L.P.

[57] ABSTRACT

A catalyst useful for the alkylation of isoalkanes is disclosed along with a process therefor the same. The catalyst comprises a reaction product resulting from mutual contact of a zirconium halide and a magnesium halide and/or a magnesium oxyhalide. The process for the alkylation of isoalkanes with alkenes is carried out in the presence of a catalyst comprising a reaction product resulting from mutual contact of a zirconium halide and a magnesium halide and/or a magnesium oxyhalide at a temperature of room temperature—150° C. and a pressure of atmospheric—5 MPa.

7 Claims, No Drawings

CATALYST FOR USE IN THE ALKYLATION OF ISOALKANES

BACKGROUND OF THE INVENTION

1. Field of the Invention

This invention relates to alkylation of isoalkanes and catalysts therefor.

2. Prior Art

In line with the global move for environmental protection, there has been considerable improvement in gasoline materials for automotive fuels which are relatively free of environmentally harmful alkenes and aromatics. A notable example of such improved gasoline material is an alkylate rich in highly branched alkane contents. Such alkylates may be derived by reacting an isoalkane with an alkene of 3–6 carbon atoms. This reaction is usually accompanied by objectionable side reactions such as isomerization, polymerization, cracking, disproportionation and so on. To eliminate or suppress these side reactions, it has been proposed to use an alkylation catalyst which comprises a relatively strong acid such as typically sulfuric acid and hydrofluoric acid. However, sulfuric acid is highly corrosive, leading to increased energy required for removal of reaction heat. Hydrofluoric acid is difficult or tedious to handle. These highly acidic catalysts have been replaced by a solid acid catalyst such as zeolite, $BF_3$ modified zeolite, Lewis acid and/or Bronsted acid supported on an inorganic carrier (such as for example $SO_4/ZrO_2$) and chlorinated alumina. However, such solid acid catalysts have a drawback when used in the alkylation of isoalkanes in that higher molar ratios of for example isobutane/alkane are needed to suppress objectionable side reactions, and another drawback in that unsaturated oligomers tend to deposit on the acid site of the catalyst to cause quick catalytic deterioration, resulting in frequent catalyst reactivation. Whereas, the use of such a zeolite as comprising a relatively weak solid acid would involve extremely high reaction temperature.

WO94/10106 discloses reacting alkenes with isoalkanes to produce alkylates in the presence of a catalyst comprising an organosulfonic acid having at least one C-F or C-P bond and a Lewis acid. The disclosed process is still disadvantageous because of the use of boron trifluoride ($BF_3$) which is highly toxic and corrosive, hence demanding extreme caution in handling the catalyst.

SUMMARY OF THE INVENTION

With the foregoing drawbacks of the prior art in view, the present invention seeks to provide such a catalyst highly eligible for use in the alkylation of isoalkanes which is easy to make and handle, non-toxious and corrosion-resistant.

The invention also seeks to provide an alkylation process in which isoalkanes are reacted with alkenes in the presence of the above catalyst to provide increased rate of alkene conversion and higher yield of highly branched isoalkane.

It has now been found that the process of the invention is highly conducive to the availability of trimethyl pentane and other components useful for high octane-number gasoline, while at the same time the inventive alkylation process involves a minimum of such objectionable heavy side products that may otherwise make the intended product reddish, thus obviating the necessity of refining the alkylate by treating with water or alkaline solution.

According to one aspect of the invention there is provided a catalyst for use in the alkylation of isoalkanes which comprises a reaction product resulting from mutual contact of a zirconium halide and a magnesium halide and/or a magnesium oxyhalide.

According to another aspect of the invention there is provided a process for the alkylation of isoalkanes with alkenes in the presence of a catalyst comprising a reaction product resulting from mutual contact of a zirconium halide and a magnesium halide and/or a magnesium oxyhalide, the process being effected at a temperature of room temperature —150° C. and a pressure of atmospheric—5 MPa.

DETAILED DESCRIPTION OF THE INVENTION

The catalyst provided in accordance with the invention results from contacting a zirconium halide with a magnesium halide and/or a magnesium oxyhalide in a paraffinic hydrocarbon solvent such as hexane and heptane substantially unreactive with the starting compounds at a temperature of 0° C.-solvent boiling point for about 15 minutes to 5 hours with or without stirring, or copulverizing the starting compounds in a mixed state importantly in the absence of oxygen and water, preferably in an inert gas atmosphere such as of nitrogen, argon and the like.

There may be used a jet-mill, vibration ball mill, rotary ball mill, disc vibration mill, rod mill, impulse mill or stirrer for the pulverization of the starting compounds which may be carried out at —10° C. -200° C., preferably 10° C. -50° C, for about 30 minutes or longer, preferably 3–24 hours, more preferably 10–16 hours. This pulverization is intended to mechanically provide the starting compounds with new surfaces, but with no particular restriction upon the particle size of the resultant pulverized product. However, when the catalyst is to be used in particulate form, its average particle size is preferably 10–200 $\mu$m, or 0.5 mm–5 mm when admixed with a binder such as silica or silica alumina.

The term starting compound as used herein refers to zirconium halide, preferably zirconium tetrahalide including zirconium tetrachloride, zirconium tetrabromide and zirconium tetraiodide, of which zirconium tetrachloride is particularly preferred, and also to magnesium halide including magnesium chloride ($MgCl_2$), magnesium bromide ($MgBr_2$) and magnesium iodide ($MgI_2$), of which magnesium chloride is particularly preferred. These magnesium halides may be anhydrous or hydrates of 2, 4, 6, 8 and 12 which are preferably sintered (prior to copulverization) at 150°–300° C. for 1–15 hours usually in the air or in nitrogen gas. The term starting compound further refers to magnesium oxyhalide which may be represented by Mg(OH)X wherein X is halogen, or a sintered product of a compound of the formula $aMgO.bMgX_2.cH_2O$ wherein X is halogen and a, b and c each are an integer.

The Mg(OH)X compound includes magnesium oxychloride [Xg(OH)Cl], magnesium oxybromide [Mg(OH)Br] and magnesium oxyiodide [Mg(OH)I]. Magnesium oxychloride [Mg(OH)Cl] may be obtained by sintering $MgCl_2.6H_2O$ at 250° C.–300° C. for about 1–15 hours.

The $aMgO.bMgX_2.cH_2O$ compound where X is chlorine typically includes $5MgO.MgCl_2.13H_2O$, $10MgO.MgCl_2.18H_2O$, $MgO.MgCl_2.H_2O[Mg(OH)Cl]$, and $MgO.MgCl_2.6H_2O$. These are sintered in the air or in nitrogen atmosphere usually at 150°–300° C. for about 1–15 hours.

In the preparation of the alkylation catalysts according to the invention, zirconium halide is contacted with magnesium halide and/or magnesium oxyhalide in an amount of generally 0.01–50, preferably 0.1–10, more preferably 0.2–5 millimols per gram of the sum of the latter. This contact product hereinafter referred to as catalyst component (A) may be used per se as the alkylation catalyst, and may be further blended with other components as described below.

The present invention also contemplates the foregoing fundamental catalyst component (A) which further comprises another catalyst component (B) comprising a sulfonic acid having a fluorine-carbon bond. Sulfonic acids of this definition include an aliphatic sulfonic acid of the formula $R^1SO_3H$ where $R^1$ is a $C_1$–$C_{20}$, preferably a $C_1$–$C_{12}$ alkyl or alkoxyalkyl group and derivatives thereof, and an aromatic sulfonic acid of the formula $R^2SO_3H$ where $R^2$ is a $C_6$–$C_{12}$, preferably a $C_6$–$C_{10}$ aryl group and derivatives thereof, part or whole of the hydrogen atoms in either of the two hydrocarbons being substituted by fluorine. Specific examples include trifluoromethane sulfonate ($CF_3SO_3H$), perfluorooctane sulfonate [$F(F_2)_8SO_3H$] and perfluoro(2-ethoxy ethane) sulfonate ($C_2H_5OCF_2CF_2SO_3H$) of which the first mentioned sulfonate is particularly preferred.

The above additional catalyst component (B), though not restrictively, is added in an amount of generally less than 50 mols, preferably 0.001–50 mols, more preferably 0.01–10 mols, most preferably 0.01–1 mol per mol of zirconium halide in the catalyst component (A).

The catalyst components (A) and (B) may be fed to the alkylation reaction system separately or after they are mixed together in advance as in the following manner and sequence.

i) the reaction system is fed first with component (A) and then component (B).

ii) The reaction system is fed first with component (B) and then component (A).

iii) Components (A) and (B) are mixed in nitrogen atmosphere and thereafter this admixture is fed to the reaction system.

iv) The reaction system is fed first with part of component (A), then with the whole of component (B) and thereafter with the remainder of component (A).

v) The reaction system is fed first with part of component (B), then with the whole of component (A) and thereafter with the remainder of component (B).

vi) The admixture of iii) is fed in batches to the reaction system. The sequence i) is particularly preferred. Components (A) and (B) may be admixed as in iii) and vi) in nitrogen atmosphere at −20° C.–50° C. for 10 minutes to 5 hours in the presence of a saturated aliphatic hydrocarbon solvent such as isobutane, butane, pentane, hexane, heptane, octane, nonane and decane, of which heptane is particularly preferred. Although the catalyst is preferably supplied to the reaction system after the solvent is removed, it may be also added in slurry form. Alternatively, components (A) and (B) may be admixed mechanically in the absence of solvents for 10 minutes to 5 hours usually in nitrogen atmosphere at −20° C.–200° C., preferably at room temperature −50° C.

The invention further contemplates admixing the fundamental catalyst component (A) which comprises a further component (C) comprising a $C_1$–$C_{24}$ hydrocarbon halide. These hydrocarbon compounds or derivatives thereof eligible for the purpose of the invention include those of a $C_1$–$C_{24}$, preferably a $C_1$–$C_{12}$ chain hydrocarbon, a $C_3$–$C_{24}$, preferably a $C_4$–$C_{12}$ alicyclic hydrocarbon and a $C_6$–$C_{12}$, preferably a $C_6$–$C_{10}$ aromatic hydrocarbon, wherein part or all of the hydrocarbon atoms in each of the hydrocarbons being substituted by halogen. Chain or alicyclic hydrocarbon halides having no unsaturated bonds (i.e. alkane or cycloalkane) are preferred. Such chain hydrocarbon halides are particularly preferred, which may be either of a straight or branched chain.

These substituting halogens may be chosen from the group of fluorine, chlorine, bromine and iodine, of which fluorine and chlorine are preferred. The number of hydrogen atoms to be substituted is between one at the minimum and as many as are substitutable by a selected halogen. The number of halogen in the hydrocarbon halides used as component (C) is usually 1–4, preferably 1–3.

Examples of the chain hydrocarbon halide eligible for use as component (C) include ethylfluoride, n-propylfluoride, isopropylfluoride, n-butylfluoride, sec-butylfluoride, tert-butylfluoride, n-pentylfluoride, isoamylfluoride, neopentylfluoride, hexylfluoride, octylfluoride, methylchloride, ethylchloride, n-propylchloride, isopropylchloride, n-butylchloride, sec-butylchloride, tert-butylchloride, n-pentylchloride, isoamylchloride, neopentylchloride, hexylchloride, octylchloride, methylbromide, ethylbromide, n-propylbromide, isopropylbromide, n-butylbromide, sec-butylbromide, tert-butylbromide, n-pentylbromide, isoamylbromide, neopentylbromide, hexylbromide, octylbromide, methyliodide, ethyliodide, n-propyliodide, isopropyliodide, n-butyliodide, sec-butyliodide, tert-butyliodide, n-pentyliodide, isoamyliodide, neopentyliodide, hexyliodide and octyliodide, of which isopropylchloride, n-butylchloride, sec-butylchloride, tert-butylchloride and neopentylchloride are particularly preferred. 1, 2-dichloroethane, trichloroethane, dichloropropane and trichloropropane are also eligible for the purpose of the invention.

Examples of the alicyclic hydrocarbon halide (C) include fluorocyclopropane, chlorocyclopropane, bromocyclopropane, iodocyclopropane, fluorocyclobutane, chlorocyclobutane, bromocyclobutane, iodocyclobutane, fluorocyclopentane, chlorocyclopentane, bromocyclopentane, iodocyclopentane, fluorocyclohexane, chlorocyclohexane, bromocyclohexane, iodocyclohexane, fluorocycloheptane, chlorocycloheptane, bromocycloheptane, iodocycloheptane, fluorocyclooctane, chlorocyclooctane, bromocyclooctane, iodocyclooctane, fluorocyclononane, chlorocyclononane, bromocyclononane, iodocyclononane, fluorocyclodecane, chlorocyclodecane, bromocyclodecane and iodocyclodecane.

Examples of the aromatic hydrocarbon halide (C) include halogenated derivatives of benzene such as monofluorobenzene, difluorobenzene, trifluorobenzene, tetrafluorobenzene, pentafluorobenzene, hexafluorobenzene, monochlorobenzene, dichlorobenzene, trichlorobenzene, tetrachlorobenzene, pentachlorobenzene, hexachlorobenzene, monobromobenzene, dibromobenzene, tribromobenzene, tetrabromobenzene, pentabromobenzene, hexabromobenzene, monoiodobenzene, diiodobenzene, triiodobenzene, tetraiodobenzene, pentaiodobenzene and hexaiodobenzene; halogenated derivative of toluene such as benzylfluoride, benzalfluoride, benztrifluoride, benzylchloride, benzalchloride, benztrichloride, benzylbromide, benzalbromide, benztribromide, benzyliodo, benzaliodo and benztriiodo; halogenated derivatives of xylene such as monofluoroxylene, difluoroxylene, monochloroxylene, dichloroxylene, monobromoxylene, dibromoxylene, monoiodoxylene and diiodoxylene. Halogenated derivatives of naphthalene such as monochloronaphthalene, dichloronaphthalene, monobromonaphthalene and dibromonaphthalene are also eligible for use in the invention.

The catalyst components (A) and (C) may be fed to the alkylation reaction system separately or after they are mixed together in advance as in the following manner and sequence.

i) the reaction system is fed first with component (A) and then component (C).

ii) The reaction system is fed first with component (C) and then component (A).

iii) Components (A) and (C) are mixed in nitrogen atmosphere and thereafter this admixture is fed to the reaction system.

iv) The reaction system is fed first with part of component (A), then with the whole of component (C) and thereafter with the remainder of component (A).

v) The reaction system is fed first with part of component (C), then with the whole of component (A) and thereafter with the remainder of component vi) The admixture of iii) is fed in batches to the reaction system. The sequence i) is particularly preferred. Components (A) and (C) may be admixed as in iii) and vi) in nitrogen atmosphere at −20° C.–50° C. for 10 minutes to 5 hours in the presence of a saturated aliphatic hydrocarbon solvent such as isobutane, butane, pentane, hexane, heptane, octane, nonane and decane, of which heptane is particularly preferred. Although the catalyst is preferably supplied to the reaction system after the solvent is removed, it may be also added in slurry form. Alternatively, components (A) and (C) may be admixed mechanically in the absence of solvents for 10 minutes to 5 hours usually in nitrogen atmosphere at −20° C.–200° C., preferably at room temperature −50° C.

The alkylation of isoalkanes according to the invention is carried out in the presence of any or either of the foregoing catalysts, in which instance alkenes are used as the alkylation agent. Eligible alkenes are of 3–6 carbon atoms, including propylene, butene-1, trans-butene-2, cis-butene-2, isobutylene, pentene-1, pentene-2, 2-methylbutene-1, 2-methylbutene-2, hexene-1, hexene-2, 2,3-dimethylbutene, 2-methylpentene-1, and 4-methylpentene-1, of which butene-1, trans-butene-2, cis-butene-2 and isobutylene are particularly preferred. Two or more of these alkenes may be used in combination.

The isoalkanes to be alkylated according to the invention are of 4–6, preferably 4–5 carbon atoms, including isobutane, isopentane and isohexane, of which isobutane is particularly preferred. These isoalkanes may be likewise used in any suitable combination.

Either of the co-reactant isoalkanes and alkenes may not necessarily be of high purity but should usually be 50%, preferably 60% in purity, and may contain other hydrocarbons or hydrogen. Their suitable source of supply is found at the site of hydrocarbon contact cracking.

The mole ratio of alkene:isoalkane in the alkylation system is usually in the range of 1:1–1:1000, preferably 1:2–1:500, more preferably 1:2–1:50. The alkylation reaction is effected usually at a temperature of room temperature −200° C., preferably 20°–150° C., more preferably 20°–125° C., still more preferably 50°–100° C., and at a pressure of atmospheric −5 MPa, preferably 0.3–2 MPa.

The alkylation process may be conducted in either liquid phase or gas phase, but preferably in liquid phase, and in either batch or continuous mode of operation. In the batch operation, the sum of alkene and isoalkane is usually in the range of 1–200 grams, preferably 5–100 grams per gram of the copulverized catalyst, although this may be further variable. Each batch operation may be effected usually for 5 minutes to 5 hours, preferably 10 minutes to 3 hours to complete the reaction.

The continuous mode of alkylation reaction according to the invention is usually conducted by supplying a feedstock (containing co-reactant isoalkane and alkene) through a catalyst bed at a liquid space velocity (LSV) of 0.01–30 $h^{-1}$, preferably 0.1–20 $h^{-1}$.

There may be used water or some lower alcohol such as methanol in the alkylation reaction system so as to provide increased alkene conversion and higher yield of branched isoalkane, but their addition should be in the range of 0.01–1.2 mols, preferably 0.1–1 mol per gram atom of zirconium.

The alkylation product may be removed for example by means of distillation of unreacted materials which may be recycled to the reaction system if desired.

Alkylation of an isoalkane with an alkene according to the invention will yield highly branched isoalkane; for instance, reacting an isobutane with butenes will result in increased yield of trimethyl pentane and other materials useful for high octane-number gasoline.

The invention will be further described by way of the following examples which are provided for illustrative purposes but not in a limiting sense.

EXAMPLE 1

Preparation of Catalyst

There was used a 400 ml stainless steel pot containing 12 pieces of ½ inch stainless steel balls and 4 pieces of 1 inch stainless steel balls. Into this pot were charged 11 grams magnesium anhydrous chloride and 6.5 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. This autoclave was charged in nitrogen atmosphere with 2.5 grams of the above catalyst, and the reaction system was cooled to −20° C., followed by charging 85 grams isobutane which had been dehydrated by Molecular Sieve 4A and also 7 grams butene-2. The alkylation reaction was allowed to continue at a pressure of 0.62 MPa after heating the system to 50° C. and thus for 2 hours with stirring. The reaction system was cooled to take out 5.1 grams product liquid which was then analyzed by gas chromatography to reveal a butene conversion of 73 mass %, a $C_8$ hydrocarbon selection of 28% and a trimethyl pentane selection of 45%. The butene conversion (mass %) is calculated from the ratio of the product to the feed butene.

EXAMPLE 2

Preparation of Catalyst a) Preparation of Mg(OH)Cl

This catalyst component was prepared by calcining 10 grams $MgCl_2 \cdot 6H_2O$ in a flow at 5 ml/min of nitrogen at 275° C. for 10 hours.

b) Copulverization of Mg(OH)Cl and $ZrCl_4$

A similar pot to that used in Example 1 was charged in nitrogen atmosphere with 3.2 grams Mg(OH)Cl obtained as above in a) and 10 grams zirconium tetrachloride. The admixture was copulverized for 16 hours.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 120 grams isobutane which had been dehydrated by Molecular Sieve 4A and also 4 grams butene-2. The alkylation reaction was allowed to continue at a pressure of 0.62 MPa after heating the system to 50° C. and thus for 2 hours with stirring. The reaction system was cooled to take out 3.4 grams product liquid. This product was then analyzed by gas chromatography to reveal a butene conversion of 85 mass %, a $C_8$ hydrocarbon selection of 35% and a trimethyl pentane selection of 48%.

EXAMPLE 3
Preparation of Catalyst

There was used a 400 ml stainless steel pot containing 12 pieces of ½ inch stainless steel balls and 4 pieces of 1 inch stainless steel balls. Into this pot were charged 10 grams magnesium anhydrous chloride and 10.8 grams zirconium tetrabromide in nitrogen atmosphere. The admixture was subjected to copulverization for 16 hours thereby obtaining a catalyst.

Alkylation of Isobutane/Butene-1

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 150 grams isobutane which had been dehydrated by Molecular Sieve 4A and also 5 grams butene-1. The alkylation reaction was allowed to continue at a pressure of 0.62 MPa after heating the system to 50° C. and thus for 2 hours with stirring. The reaction system was cooled to take out 4.4 grams product liquid. This product was then analyzed by gas chromatography to reveal a butene conversion of 89 mass %, a $C_8$ hydrocarbon selection of 25% and a trimethyl pentane selection of 18%.

EXAMPLE 4
Preparation of Catalyst

There was used a 400 ml stainless steel pot containing 12 pieces of ½ inch stainless steel balls and 4 pieces of 1 inch stainless steel balls. Into this pot were charged 10 grams magnesium anhydrous chloride and 1.5 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 200 grams isobutane which had been dehydrated by Molecular Sieve 4A and also 5 grams butene-2. The alkylation reaction was allowed to continue at a pressure of 1.0 MPa after heating the system to 70° C. and thus for 2 hours with stirring. The reaction system was cooled to take out 4.3 grams product liquid. This product was then analyzed by gas chromatography to reveal a butene conversion of 85 mass %, a $C_8$ hydrocarbon selection of 40% and a trimethyl pentane selection of 47%.

EXAMPLE 5
Preparation of Catalyst

There was used a 400 ml stainless steel pot containing 12 pieces of ½ inch stainless steel balls and 4 pieces of 1 inch stainless steel balls. Into this pot were charged 10 grams Mg(OH)Cl which was prepared in accordance with the procedure of Example 2 and 6.1 grams zirconium tetrachloride in nitrogen atmosphere. The admixture was subjected to copulverization for 16 hours thereby obtaining a catalyst.

Alkylation of Isobutane/Butene-2

There was used a 300 ml autoclave equipped with an electromagnetic induction type stirrer. The autoclave was charged in nitrogen atmosphere with 2.5 grams of the above catalyst, and the reaction system was cooled to −20° C., followed by charging 85 grams isobutane which had been dehydrated by Molecular Sieve 4A and also 15 grams butene-2. The alkylation reaction was allowed to continue at a pressure of 0.35 MPa after heating the system to 30° C. and thus for 2 hours with stirring. The reaction system was cooled to take out 7.3 grams product liquid. This product was then analyzed by gas chromatography to reveal a butene conversion of 49 mass %, a $C_8$ hydrocarbon selection of 20% and a trimethyl pentane selection of 25%.

EXAMPLE 6
Alkylation of Isobutane/Butene-2

There was used a 300 ml autoclave equipped with an electromagnetic induction type stirrer. The autoclave was charged in nitrogen atmosphere with 2.5 grams of the catalyst of Example 1, and the reaction system was cooled to −20° C., followed by charging 100 grams isobutane which had been dehydrated by Molecular Sieve 4A and also 5 grams butene-2. The reaction system was again cooled to −20° C. and then added in. nitrogen atmosphere with 50 micro liter water. The alkylation reaction was allowed to continue at a pressure of 0.6 MPa after heating the system to 50° C. and thus for 2 hours with stirring. The reaction system was cooled to take out 4.4 grams product liquid. This product was then analyzed by gas chromatography to reveal a butene conversion of 87 mass %, a $C_8$ hydrocarbon selection of 38% and a trimethyl pentane selection of 49%.

EXAMPLE 7
Preparation of Catalyst a) Calcination of $MgO.MgCl_2.6H_2O$ 10 grams $MgO.MgCl_2.6H_2O$ was calcined in a flow at 5 ml/min of nitrogen at 275° C. for 10 hours.

b) Copulverization of calcined MgO. $MgCl_2.6H_2O$ and $ZrCl_4$

A similar pot to that used in Example 1 was charged in nitrogen atmosphere with 10 grams $MgO.MgCl_2.6H_2O$ obtained as above in a) and 10 grams zirconium tetrachloride. The admixture was copulverized for 16 hours.

Alkylation of Isobutane/Butene-2

There was used a 300 ml autoclave equipped with an electromagnetic induction type stirrer. The autoclave was charged in nitrogen atmosphere with 3.5 grams of the above catalyst, and the reaction system was cooled to −20° C., followed by charging 100 grams isobutane which had been dehydrated by Molecular Sieve 4A and also 5 grams butene-2. The alkylation reaction was allowed to continue at a pressure of 0.62 MPa after heating the system to 50° C. and thus for 2 hours with stirring. The reaction system was cooled to take out 3.4 grams product liquid. This product was then analyzed by gas chromatography to reveal a butene conversion of 61 mass %, a $C_8$ hydrocarbon selection of 23% and a trimethyl pentane selection of 37%.

COMPARATIVE EXAMPLE 1
Alkylation of Isobutane/Butene-2

There was used a 300 ml autoclave equipped with an electromagnetic induction type stirrer. The autoclave was charged in nitrogen atmosphere with 2.5 grams of zirconium tetrachloride, and the reaction system was cooled to −20° C., followed by charging 85 grams isobutane which had been dehydrated by Molecular Sieve 4A and also 7 grams butene- 2. The alkylation reaction was allowed to continue at a pressure of 0.62 MPa after heating the system to 50° C. and thus for 2 hours with stirring. The reaction system was cooled to take out 2.1 grams product liquid. This product was then analyzed by gas chromatography to reveal a butene conversion of 30 mass %, a $C_8$ hydrocarbon selection of 16% and a trimethyl pentane selection of 25.5%

EXAMPLE 8

Preparation of Catalyst Component (A)

There was used a 400 ml stainless steel pot containing 12 pieces of ½ inch stainless steel balls and 4 pieces of 1 inch stainless steel balls. Into this pot were charged 3.4 grams magnesium anhydrous chloride and 6.5 grams zirconium tetrachloride in nitrogen atmosphere. The admixture was subjected to copulverization for 16 hours thereby obtaining catalyst component (A).

Alkylation of Isobutane/Butene-2

There was used a 300 ml autoclave equipped with an electromagnetic induction type stirrer. The autoclave was charged in nitrogen atmosphere with 2.0 grams of the above catalyst component (A), and the reaction system was cooled to −20° C., followed by charging 85 grams isobutane which had been dehydrated by Molecular Sieve 4A and also 10 grams butene-2. The admixture was then charged with 0.6 grams of catalyst component (B) ($CF_3SO_3H$). The alkylation reaction was allowed to continue at a pressure of 0.62 MPa after heating the system to 50° C. and thus for 2 hours with stirring. The reaction system was cooled to take out 9 grams product liquid. This product was then analyzed by gas chromatography to reveal a butene conversion of 90 mass %, a $C_8$ hydrocarbon selection of 45% and a trimethyl pentane selection of 61%.

EXAMPLE 9

Alkylation of Isobutane/Butene-2

There was used a 300 ml autoclave equipped with an electromagnetic induction type stirrer. The autoclave was charged in nitrogen atmosphere with 3.5 grams of catalyst component (A) of Example 8, and the reaction system was cooled to −20° C., followed by charging 150 grams isobutane which had been dehydrated by Molecular Sieve 4A and also 3 grams butene-2. The admixture was then charged with 0.7 grams of catalyst component (B) ($CF_3SO_3H$). The alkylation reaction was allowed to continue at a pressure of 1.0 MPa after heating the system to 70° C. and thus for 2 hours with stirring. The reaction system was cooled to take out 2.8 grams product liquid. This product was then analyzed by gas chromatography to reveal a butene conversion of 94 mass %, a $C_8$ hydrocarbon selection of 60% and a trimethyl pentane selection of 67%.

EXAMPLE 10

Preparation of Catalyst Component (A)

There was used a 400 ml stainless steel pot containing 12 pieces of ½ inch stainless steel balls and 4 pieces of 1 inch stainless steel balls. Into this pot were charged 6.5 grams magnesium anhydrous chloride and 6.5 grams zirconium tetrachloride in nitrogen atmosphere. The admixture was subjected to copulverization for 16 hours thereby obtaining catalyst component (A).

Alkylation of Isobutane/Butene-1

There was used a 300 ml autoclave equipped with an electromagnetic induction type stirrer. The autoclave was charged in nitrogen atmosphere with 2.5 grams of the above catalyst component (A), and the reaction system was cooled to −20° C., followed by charging 100 grams isobutane which had been dehydrated by Molecular Sieve 4A and also 15 grams butene-1. The admixture was then charged with 0.6 grams of catalyst component (B) ($CF_3SO_3H$). The alkylation reaction was allowed to continue at a pressure of 0.61 MPa after heating the system to 50° C. and thus for 2 hours with stirring. The reaction system was cooled to take out 15 grams product liquid. This product was then analyzed by gas chromatography to reveal a butene conversion of 100 mass %, a $C_8$ hydrocarbon selection of 31% and a trimethyl pentane selection of 36%.

EXAMPLE 11

Alkylation of Isobutane/Butene-2

There was used a 300 ml autoclave equipped with an electromagnetic induction type stirrer. The autoclave was charged in nitrogen atmosphere with 4.5 grams of catalyst component (A) of Example 9, and the reaction system was cooled to −20° C., followed by charging 120 grams isobutane which had been dehydrated by Molecular Sieve 4A and also 4 grams butene-2. The admixture was then charged with 2.1 grams of catalyst component (B) ($CF_3SO_3H$). The alkylation reaction was allowed to continue at a pressure of 0.61 MPa after heating the system to 50° C. and thus for 2 hours with stirring. The reaction system was cooled to take out 3.4 grams product liquid. This product was then analyzed by gas chromatography to reveal a butene conversion of 85 mass %, a $C_8$ hydrocarbon selection of 75% and a trimethyl pentane selection of 57%.

EXAMPLE 12

Preparation of Catalyst a) Preparation of Mg(OH)Cl

This catalyst component was prepared by calcining 10 grams $MgCl_2.6H_2O$ in a flow at 5 ml/min of nitrogen at 275° C. for 10 hours.

b) Copulverization of Mg(OH)Cl and $ZrCl_4$

A similar pot to that used in Example 1 was charged in nitrogen atmosphere with 3.2 grams Mg(OH)Cl obtained as above in a) and 10 grams zirconium tetrachloride. The admixture was copulverized for 16 hours.

Alkylation of Isobutane/Butene-2

There was used a 300 ml autoclave equipped with an electromagnetic induction type stirrer. The autoclave was charged in nitrogen atmosphere with 2.5 grams of the above catalyst component (A), and the reaction system was cooled to −20° C., followed by charging 150 grams isobutane which had been dehydrated by Molecular Sieve 4A and also 3 grams butene-2. The admixture was then charged with 0.6 grams of catalyst component (B) ($CF_3SO_3H$). The alkylation reaction was allowed to continue at a pressure of 0.62 MPa after heating the system to 50° C. and thus for 2 hours with stirring. The reaction system was cooled to take out 2.8 grams product liquid. This product was then analyzed by gas chromatography to reveal a butene conversion of 92 mass %, a $C_8$ hydrocarbon selection of 62% and a trimethyl pentane selection of 60%.

EXAMPLE 13

Preparation of Catalyst Component (A)

There was used a 400 ml stainless steel pot containing 12 pieces of ½ inch stainless steel balls and 4 pieces of 1 inch stainless steel balls. Into this pot were charged 10 grams magnesium anhydrous chloride and 10.8 grams zirconium tetrabromide in nitrogen atmosphere. The admixture was subjected to copulverization for 16 hours thereby obtaining catalyst component (A).

Alkylation of Isobutane/Butene-2

There was used a 300 ml autoclave equipped with an electromagnetic induction type stirrer. The autoclave was charged in nitrogen atmosphere with 2.5 grams of the above a catalyst component (A), and the reaction system was cooled to −20° C., followed by charging 84 grams isobutane which had been dehydrated by Molecular Sieve 4A and also 10 grams butene-2. The admixture was then charged with 0.6 grams of catalyst component (B) ($CF_3SO_3H$). The alkylation reaction was allowed to continue at a pressure of 0.62 MPa after heating the system to 50° C. and thus for 2 hours with stirring. The reaction system was cooled to take out 5.3 grams product liquid. This product was then analyzed by gas chromatography to reveal a butene conversion of 53 mass %, a $C_8$ hydrocarbon selection of 30% and a trimethyl pentane selection of 28%.

EXAMPLE 14
Preparation of Catalyst Component (A)
a) Calcination of MgO. $MgCl_2.6H_2O$
10 grams $MgO.MgCl_2.6H_2O$ was calcined in a flow at 5 ml/min of nitrogen at 275° C. for 10 hours.
b) Copulverization of calcined $MgO.MgCl_2.6H_2O$ and $ZrCl_4$
A similar pot to that used in Example 1 was charged in nitrogen atmosphere with 10 grams $MgO.MgCl_2.6H_2O$ obtained as above in a) and 10 grams zirconium tetrachloride. The admixture was copulverized for 16 hours.

Alkylation of Isobutane/Butene-2
There was used a 300 ml autoclave equipped with an electromagnetic induction type stirrer. The autoclave was charged in nitrogen atmosphere with 10 grams of the above catalyst component (A), and the reaction system was cooled to −20° C., followed by charging 100 grams isobutane which had been dehydrated by Molecular Sieve 4A and also 5 grams butene-2. The admixture was then charged with 0.65 grams of catalyst component (B) ($CF_3SO_3H$). The alkylation reaction was allowed to continue at a pressure of 0.62 MPa after heating the system to 50° C. and thus for 2 hours with stirring. The reaction system was cooled to take out 3.1 grams product liquid. This product was then analyzed by gas chromatography to reveal a butene conversion of 62 mass %, a $C_8$ hydrocarbon selection of 50% and a trimethyl pentane selection of 58%.

EXAMPLE 15
Preparation of Catalyst Component (A)
There was used a 400 ml stainless steel pot containing 12 pieces of ½ inch stainless steel balls and 4 pieces of 1 inch stainless steel balls. Into this pot were charged 10 grams magnesium anhydrous chloride and 2.5 grams zirconium tetrachloride in nitrogen atmosphere. The admixture was subjected to copulverization for 16 hours thereby obtaining catalyst component (A).

Alkylation of Isobutane/Butene-2
There was used a 300 ml autoclave equipped with an electromagnetic induction type stirrer. The autoclave was charged in nitrogen atmosphere with 3.0 grams of the above catalyst, and the reaction system was cooled to −20° C., followed by charging 85 grams isobutane which had been dehydrated by Molecular Sieve 4A and also 10 grams butene-2. The admixture was then charged with 0.1 grams of catalyst component (B) ($CF_3SO_3H$). The alkylation reaction was allowed to continue at a pressure of 0.62 MPa after heating the system to 50° C. and thus for 2 hours with stirring. The reaction system was cooled to take out 9.2 grams product liquid. This product was then analyzed by gas chromatography to reveal a butene conversion of 92 mass %, a $C_8$ hydrocarbon selection of 48% and a trimethyl pentane selection of 64%.

COMPARATIVE EXAMPLE 2
Alkylation of Isobutane/Butene-2
There was used a 300 ml autoclave equipped with an electromagnetic induction type stirrer. The autoclave was was cooled to −20° C., followed by charging 85 grams isobutane which had been dehydrated by Molecular Sieve 4A and 7 grams butene-2. The admixture was then charged with 2.6 grams of catalyst component (B) ($CF_3SO_3H$). The alkylation reaction was allowed to continue at a pressure of 0.62 MPa after heating the system to 50° C. and thus for 2 hours with stirring. This liquid was washed with pure water and then with aqueous caustic soda solution. The liquid was then washed with pure water again thereby obtaining opaque liquid. The reaction system was cooled to take out 2.6 grams reddish product liquid. This product was then analyzed by gas chromatography to reveal a butene conversion of 33 mass %, a $C_8$ hydrocarbon selection of 85% and a trimethyl pentane selection of 52%

EXAMPLE 16
Preparation of Catalyst Component (A)
There was used a 400 ml stainless steel pot containing 12 pieces of ½ inch stainless steel balls and 4 pieces of 1 inch stainless steel balls. Into this pot were charged 11 grams magnesium anhydrous chloride and 6.5 grams zirconium tetrachloride in nitrogen atmosphere. The admixture was subjected to copulverization for 16 hours thereby obtaining catalyst component (A).

Alkylation of Isobutane/Butene-2
There was used a 300 ml autoclave equipped with an electromagnetic induction type stirrer. The autoclave was charged in nitrogen atmosphere with 3.4 grams of the above catalyst component (A), and the reaction system was cooled to −20° C., followed by charging 100 grams isobutane which had been dehydrated by Molecular Sieve 4A and also 7 grams butene-2. The admixture was then charged with 1.2 ml of catalyst component (C) (tert-butylchloride). The alkylation reaction was allowed to continue at a pressure of 0.62 MPa after heating the system to 50° C. and thus for 2 hours with stirring. The reaction system was cooled to take out 7.4 grams product liquid. This product was then analyzed by gas chromatography to reveal a butene conversion of 106 mass %, a $C_8$ hydrocarbon selection of 43% and a trimethyl pentane selection of 73%.

EXAMPLE 17
Preparation of Catalyst Component (A)
There was used a 400 ml stainless steel pot containing 12 pieces of 112 inch stainless steel balls and 4 pieces of 1 inch stainless steel balls. Into this pot were charged 11 grams magnesium anhydrous chloride and 13.5 grams zirconium tetrachloride in nitrogen atmosphere. The admixture was subjected to copulverization for 16 hours thereby obtaining catalyst component (A).

Alkylation of Isobutane/Butene-2
There was used a 300 ml autoclave equipped with an electromagnetic induction type stirrer. The autoclave was charged in nitrogen atmosphere with 10 grams of the above catalyst component (A), and the reaction system was cooled to −20° C., followed by charging 150 grams isobutane which had been dehydrated by Molecular Sieve 4A and also 3 grams butene-2. The admixture was then charged with 2.6 ml of catalyst component (C) (tert-butylchloride). The alkylation reaction was allowed to continue at a pressure of 1.0 MPa after heating the system to 70° C. and thus for 2 hours with stirring. The reaction system was cooled to take out 3.3 grams product liquid. This product was then analyzed by gas chromatography to reveal a butene conversion of 110 mass %, a $C_8$ hydrocarbon selection of 52% and a trimethyl pentane selection of 75%.

EXAMPLE 18
Alkylation of Isobutane/Butene-2

There was used a 300 ml autoclave equipped with an electromagnetic induction type stirrer. The autoclave was charged in nitrogen atmosphere with 7.8 grams of catalyst component (A) of Example 16, and the reaction system was cooled to −20° C., followed by charging 100 grams isobutane which had been dehydrated by Molecular Sieve 4A and also 12 grams a mixture of buten isomers (buten-1/cis-buten-2/trans-buten-2=7%/29%/64%). The admixture was then charged with 0.7 ml of catalyst component (C) (tert-butylchloride). The alkylation reaction was allowed to continue at a pressure of 0.61 MPa after heating the system to 50° C. and thus for 2 hours with stirring. The reaction system was cooled to take out 12 grams product liquid. This product was then analyzed by gas chromatography to reveal a butene conversion of 100 mass %, a $C_8$ hydrocarbon selection of 39% and a trimethyl pentane selection of 69%.

EXAMPLE 19
Preparation of Catalyst a) Preparation of Mg(OH)Cl

This catalyst component was prepared by calcining 10 grams $MgCl_2.6H_2O$ in a flow at 5 ml/min of nitrogen at 275° C. for 10 hours.

b) Copulverization of Mg(OH)Cl and $ZrCl_4$

A similar pot to that used in Example 1 was charged in nitrogen atmosphere with 3.2 grams Mg(OH)Cl obtained as above in a) and 10 grams zirconium tetrachloride. The admixture was copulverized for 16 hours.

Alkylation of Isobutane/Butene-2

There was used a 300 ml autoclave equipped with an electromagnetic induction type stirrer. The autoclave was charged in nitrogen atmosphere with 2.5 grams of the above catalyst component (A), and the reaction system was cooled to −20° C., followed by charging 120 grams isobutane which had been dehydrated by Molecular Sieve 4A and also 6 grams butene-2. The admixture was then charged with 0.9 ml of catalyst component (C) (tert-butylchloride). The alkylation reaction was allowed to continue at a pressure of 0.62 MPa after heating the system to 50° C. and thus for 2 hours with stirring. The reaction system was cooled to take out 5.4 grams product liquid. This product was then analyzed by gas chromatography to reveal a butene conversion of 90 mass %, a $C_8$ hydrocarbon selection of 45% and a trimethyl pentane selection of 65%.

EXAMPLE 20
Alkylation of Isobutane/Butene-2

There was used a 300 ml autoclave equipped with an electromagnetic induction type stirrer. The autoclave was charged in nitrogen atmosphere with 3.7 grams of catalyst component (A) of Example 16, and the reaction system was cooled to −20° C., followed by charging 100 grams isobutane which had been dehydrated by Molecular Sieve 4A and also 5 grams butene-2. The admixture was then charged with 0.7 g of catalyst component (C) (benzylchloride). The alkylation reaction was allowed to continue at a pressure of 0.61 MPa after heating the system to 50° C. and thus for 2 hours with stirring. The reaction system was cooled to take out 5.4 grams product liquid. This product was then analyzed by gas chromatography to reveal a butene conversion of 108 mass %, a $C_8$ hydrocarbon selection of 43% and a trimethyl pentane selection of 53%.

EXAMPLE 21
Preparation of Catalyst Component (A)

There was used a 400 ml stainless steel pot containing 12 pieces of ½ inch stainless steel balls and 4 pieces of 1 inch stainless steel balls. Into this pot were charged 10 grams magnesium anhydrous chloride and 10.8 grams of zirconium tetrabromide in nitrogen atmosphere. The admixture was subjected to copulverization for 16 hours thereby obtaining catalyst component (A).

Alkylation of Isobutane/Butene-2

There was used a 300 ml autoclave equipped with an electromagnetic induction type stirrer. The autoclave was charged in nitrogen atmosphere with 3 grams of the above catalyst component (A), and the reaction system was cooled to −20° C., followed by charging 85 grams isobutane which had been dehydrated by Molecular Sieve 4A and also 10 grams butene-2. The admixture was then charged with 1.4 g of catalyst component (C) (neopentylchloride). The alkylation reaction was allowed to continue at a pressure of 0.62 MPa after heating the system to 50° C. and thus for 2 hours with stirring. The reaction system was cooled to take out 7 grams product liquid. This product was then analyzed by gas chromatography to reveal a butene conversion of 70 mass %, a $C_8$ hydrocarbon selection of 30% and a trimethyl pentane selection of 39%.

EXAMPLE 22
Preparation of Catalyst Component (A)

a) Calcination of $MgO.MgCl_2.6H_2O$ 10 grams $MgO.MgCl_2.6H_2O$ was calcined in a flow at 5 ml/min of nitrogen at 275° C. for 10 hours.

b) Copulverization of calcined $MgO.MgCl_2.6H_2O$ and $ZrCl_4$

A similar pot to that used in Example 1 was charged in nitrogen atmosphere with 10 grams $MgO.MgCl_2.6H_2O$ obtained as above in a) and 10 grams zirconium tetrachloride. The admixture was copulverized for 16 hours.

Alkylation of Isobutane/Butene-2

There was used a 300 ml autoclave equipped with an electromagnetic induction type stirrer. The autoclave was charged in nitrogen atmosphere with 5.3 grams of the above catalyst component (A), and the reaction system was cooled to −20° C., followed by charging 100 grams isobutane which had been dehydrated by Molecular Sieve 4A and also 5 grams butene-2. The admixture was then charged with 1 gram of catalyst component (C) (n-butylchloride). The alkylation reaction was allowed to continue at a pressure of 0.62 MPa after heating the system to 50° C. and thus for 2 hours with stirring. The reaction system was cooled to take out 3.4 grams product liquid. This product was then analyzed by gas chromatography to reveal a butene conversion of 68 mass %, a $C_8$ hydrocarbon selection of 40% and a trimethyl pentane selection of 58%.

EXAMPLE 23
Preparation of Catalyst Component (A)

There was used a 400 ml stainless steel pot containing 12 pieces of ½ inch stainless steel balls and 4 pieces of 1 inch stainless steel balls. Into this pot were charged 10 grams magnesium anhydrous chloride and 2.5 grams zirconium tetrachloride in nitrogen atmosphere. The admixture was subjected to copulverization for 16 hours thereby obtaining catalyst component (A).

Alkylation of Isobutane/Butene-2

There was used a 300 ml autoclave equipped with an electromagnetic induction type stirrer. The autoclave was charged in nitrogen atmosphere with 5.3 grams of the above catalyst component (A), and the reaction system was cooled to −20° C., followed by charging 100 grams isobutane which had been dehydrated by Molecular Sieve 4A and also 5 grams butene-2. The admixture was then charged with 2 ml of catalyst component (C) (tert-butylchloride). The alkylation reaction was allowed to continue at a pressure of 0.62 MPa after heating the system to 50° C. and thus for 2 hours with stirring. The reaction system was cooled to take out 4.8 grams product liquid. This product was then analyzed by gas chromatography to reveal a butene conversion of 95 mass %, a $C_8$ hydrocarbon selection of 38% and a trimethyl pentane selection of 51%.

COMPARATIVE EXAMPLE 3

Alkylation of Isobutane/Butene-2

There was used a 300 ml autoclave equipped with an electromagnetic induction type stirrer. The autoclave was charged in nitrogen atmosphere with 3.2 grams of catalyst component (A) of Example 16, and the reaction system was cooled to −20° C., followed by charging 100 grams isobutane which had been dehydrated by Molecular Sieve 4A and also 7 grams butene-2. The alkylation reaction was allowed to continue at a pressure of 0.62 MPa after heating the system to 50° C. and thus for 2 hours with stirring. The reaction system was cooled to take out 4.3 grams product liquid. This product was then analyzed by gas chromatography to reveal a butene conversion of 62 mass %, a $C_8$ hydrocarbon selection of 32% and a trimethyl pentane selection of 43%

What is claimed is:

1. A catalyst for use in the alkylation of isoalkanes which comprises a product resulting from copulverization of a zirconium halide and a magnesium halide and/or a magnesium oxyhalide.

2. A catalyst according to claim 1 which further comprises a sulfonic acid having a fluorine-carbon bond.

3. A catalyst according to claim 2 in which said sulfonic acid is an aliphatic sulfonic acid of the formula $R^1SO_3H$ where $R^1$ is a $C_1$–$C_{20}$ alkyl or alkoxyalkyl group or an aromatic sulfonic acid of the formula $R^2SO_3H$ where $R^2$ is a $C_6$–$C_{12}$ aryl group wherein $R^1$ and $R^2$ contain at least one fluorine atom substituent.

4. A catalyst according to claim 1 which further comprises a $C_1$–$C_{24}$ hydrocarbon halide.

5. A catalyst according to claim 4 in which said hydrocarbon halide is selected from the group consisting of a chain hydrocarbon halide, an alicyclic hydrocarbon halide and an aromatic hydrocarbon halide.

6. A catalyst according to claim 5 in which said chain or alicyclic hydrocarbon halides has no unsaturated bonds.

7. A catalyst according to claim 1, wherein the copulverization is conducted in an inert gas atmosphere at a temperature of from −10° C. to 200° C. for more than 30 minutes.

* * * * *